US009005418B2

(12) United States Patent
Belisle

(10) Patent No.: US 9,005,418 B2
(45) Date of Patent: Apr. 14, 2015

(54) MODIFIED ELECTRODE BUFFERS FOR STAIN-FREE PROTEIN DETECTION IN ELECTROPHORESIS

(71) Applicant: Bio-Rad Laboratories, Inc., Hercules, CA (US)

(72) Inventor: Christopher Belisle, Walnut Creek, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 13/961,626

(22) Filed: Aug. 7, 2013

(65) Prior Publication Data

US 2014/0042027 A1    Feb. 13, 2014

Related U.S. Application Data

(60) Provisional application No. 61/680,587, filed on Aug. 7, 2012.

(51) Int. Cl.
*G01N 27/447* (2006.01)

(52) U.S. Cl.
CPC .... *G01N 27/44726* (2013.01); *G01N 27/44713* (2013.01); *G01N 27/44747* (2013.01)

(58) Field of Classification Search
USPC ............................ 204/456, 461, 464, 489, 600
See application file for complete search history.

(56) References Cited

U.S. PATENT DOCUMENTS

| 7,056,426 | B2 | 6/2006 | Panattoni |
| 7,569,130 | B2 | 8/2009 | Edwards et al. |
| 8,007,646 | B2 | 8/2011 | Edwards et al. |
| 2006/0207881 | A1 | 9/2006 | Kovalska et al. |
| 2010/0089753 | A1* | 4/2010 | Edwards et al. .............. 204/461 |

OTHER PUBLICATIONS

Mini-Protean II Electrophoresis Cell Instruction Manual, Bio-Rad, 2005.*
International Search Report and Written Opinion from PCT/US2013/053986, mailed Dec. 2, 2013.
Edwards et al.; "The light-induced reactions of tryptophan with halocompounds"; *Photochem. & Photobiol.* 75:362-368 (2002).
Kazmin et al.; "Visualization of proteins in acrylamide gets using ultraviolet illumination"; *Anal. Biochem*: 301:91-96 (2002).
Ladner et al.; "Visible fluorescent detection of proteins in polyacrylamide gels without staining"; *Anal. Biochem*: 326:13-20 (2004).
Roegener et al.; "Ultrasensitive Detection of Unstained Proteins in Acrylamide Gels By Native UV Fluorescence", *Anal. Chem.*; 75:157-159 (2003).

* cited by examiner

*Primary Examiner* — J. Christopher Ball
(74) *Attorney, Agent, or Firm* — Kilpatrick Townsend & Stockton LLP

(57) ABSTRACT

Proteins that are electrophoretically separated in a gel are derivatized to produce fluorescent emissions by incorporating halo-substituted organic compounds into one or both of the electrode buffer solutions at the two ends of the gel. The halo-substituted compounds used are ones that bear an electric charge at the pH of the buffer solutions and gel, and the polarity of the charge on the compounds is such that the compounds migrate from the electrode buffer into the gel under the electrophoretic influence concurrently with the migration of the proteins into the gel. Once the proteins are separated and distributed within the gel and the gel is fully penetrated with the halo-substituted compounds, the gel is irradiated with ultraviolet light to induce a reaction between the halo-substituted compounds and the proteins through the tryptophan residues on the proteins, producing fluorescent reaction products.

17 Claims, 4 Drawing Sheets

MODIFIED ELECTRODE BUFFERS FOR STAIN-FREE PROTEIN DETECTION IN ELECTROPHORESIS

CROSS-REFERENCES TO RELATED APPLICATIONS

The present application claims priority to U.S. Provisional Patent Application No. 61/680,587, entitled "MODIFIED ELECTRODE BUFFERS FOR STAN-FREE PROTEIN DETECTION IN ELECTROPHORESIS" and filed Aug. 7, 2012, the entire contents of which are incorporated by reference herein for all purposes.

BACKGROUND OF THE INVENTION

Gel electrophoresis, most notably in polyacrylamide gels, is one of the most common laboratory techniques for analyzing biological samples for their protein contents, including both identification and quantitation. Detections of proteins in gels are achieved in a variety of ways. The most common is the use of stains such as COOMASSIE™ Brilliant Blue (BASF Aktiengesellschaft, Ludwigshafen, Germany), Ponceau S (Sigma-Aldrich, St. Louis, Mo., USA), and SYPRO RUBY™ (Life Technologies). Detection can also be achieved without stains, such as by using a stain-free technique disclosed by Edwards et al. in U.S. Pat. No. 7,569,103 B2 (Aug. 4, 2009) and U.S. Pat. No. 8,007,646 B2 (Aug. 30, 2011). These patents describe the UV light-induced reaction between the indole moiety of tryptophan and any of various halo-substituted organic compounds to produce a fluorescent derivative of the protein that emits light at wavelengths in the near-ultraviolet and visible range. The stain-free technique thus entails contacting the proteins or the gel with the halogen-containing reagent, exposing the gel to UV light once the proteins have been separated in bands within the gel by electrophoresis, and detecting, or forming an image of, the emissions from the proteins.

BRIEF SUMMARY OF THE INVENTION

It has now been discovered that a halo-substituted organic compound that reacts with tryptophan residues can be distributed through a gel for reaction with proteins in the gel by imposing an electric charge on the compound and incorporating the charged compound in one or both of the electrode buffers in an electrophoresis system. When a biological sample is loaded onto the gel and the electrodes that are immersed in the buffers are energized at the appropriate polarities to cause electrophoretic separation of the proteins in the sample to occur, the halo-substituted compound will migrate into and through the gel by virtue of its charge, thereby utilizing the electrophoretic principle to transfer the compound from the electrode buffer into the gel. The penetration of the gel with the halo-substituted compound will thus occur concurrently with the reparatory migration of the proteins within the gel, avoiding any need for pre-treatment of the sample or the gel or for post-treatment of the gel.

A method is provided herein for separating proteins contained within a biological sample by electrophoresis in a gel along a linear dimension between first and second ends of the gel and detecting the proteins so separated. The method includes the steps of: (a) loading the sample onto the gel and electrically connecting the first and second ends of the gel with electrodes through electrode buffers in which the electrodes are immersed, wherein at least one of the electrode buffers has suspended therein a halo-substituted organic compound that reacts with tryptophan residues upon irradiation with ultraviolet light to form fluorescent compounds, the halo-substituted organic compound bearing an electrical charge, (b) energizing the electrodes to opposing polarities in a direction selected to cause the proteins to distribute within the gel along the linear dimension and to cause the halo-substituted organic compound to migrate into the gel from the electrode buffer, and (c) with the proteins so distributed and the halo-substituted organic compound having so migrated into the gel, irradiating the gel with ultraviolet light to react tryptophan residues on the proteins with the halo-substituted organic compound to form fluorescent derivatives of the proteins and detecting fluorescent signals emitted from said fluorescent derivatives.

In some embodiments of the method, the halo-substituted organic compound bears a negative charge and step (b) includes energizing the electrode that is immersed in the electrode buffer in which the halo-substituted organic compound is suspended as a cathode. In one such embodiment, the halo-substituted organic compound has a molecular structure that contains a negative ionic moiety. In other such embodiments, the halo-substituted organic compound is a hydrophobic compound encapsulated in a negatively charged micelle. In one of these embodiments, the micelle is formed of sodium dodecyl sulfate.

In some embodiments of the method, the halo-substituted organic compound bears a positive charge and step (b) includes energizing the electrode that is immersed in the electrode buffer in which said halo-substituted organic compound is suspended as an anode. In some embodiments, the electrodes at the first and second ends of the gel are immersed in the same electrode buffer.

Also provided herein is a method of detecting proteins in an electrophoresis gel. The method includes the steps of: loading the proteins into the electrophoresis gel; placing the electrophoresis gel between two electrodes; contacting the electrophoresis gel and one or both electrodes with an electrode buffer, the electrode buffer containing a halo-substituted organic compound; energizing the electrodes to opposite polarities, thereby causing migration of proteins within the gel and transfer of the halo-substituted organic compound from the electrode buffer into the electrophoresis gel; exposing the electrophoresis gel to ultraviolet light; and detecting fluorescence emitted from the electrophoresis gel, thereby detecting proteins in the electrophoresis gel.

Some embodiments of the present methods also involve transferring proteins from the electrophoresis gel to a blotting membrane using electroblotting; exposing the blotting membrane to ultraviolet light; and detecting fluorescence emitted from the blotting membrane, thereby detecting proteins on the blotting membrane.

BRIEF DESCRIPTIONS OF THE DRAWINGS

DETAILED DESCRIPTION OF SELECTED EMBODIMENTS

Figure 1:
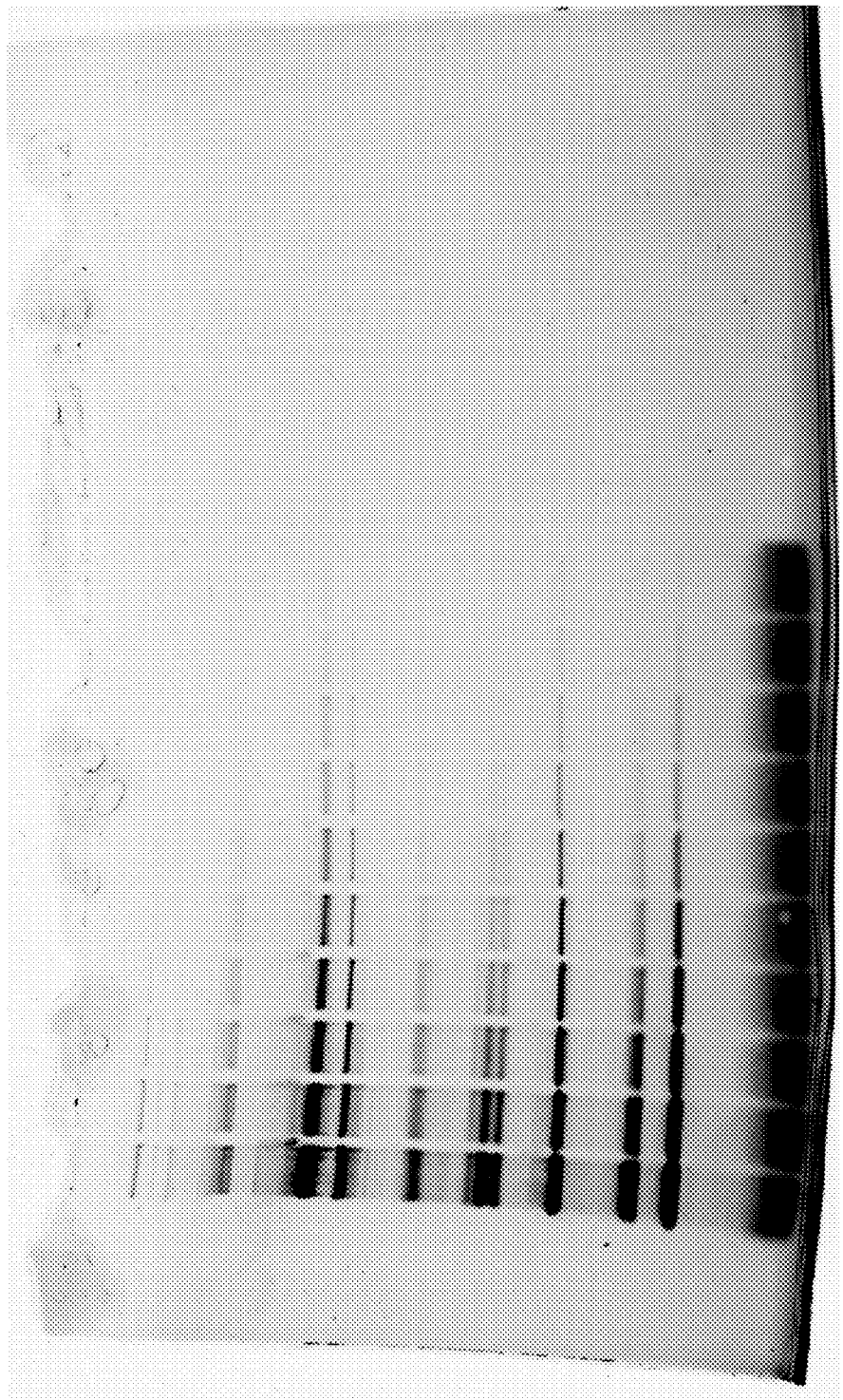
FIG. 1 shows fluorescence emitted by proteins in Gel A of the Example. Gel A contained 0.5% trichloroethanol, which was incorporated into the gel upon pouring.

A variety of halo-substituted organic compounds, and indeed any halo-substituted organic compound can be used that will enter into a chemical reaction with tryptophan to form a product that fluoresces upon exposure to excitation light, can be used in the practice of this invention. Halo-substituted organic compounds of particular interest are trihalo compounds, most notably those with molecular weights of 200 or less. Trihaloaliphatic alcohols, trihaloaliphatic acids, trihaloaliphatic amines, and trihaloalkanes are all useful. The halogen substitution can be any halogen, the most convenient of which will most likely be chlorine and bromine. When two or more halogen atoms are present on a single molecule of the compound, the halogens can be the same or a combination of different halogens. Halo-substituted organic compounds can be used individually or in combinations, such as for example combinations of two or three such compounds in approximately equal molar proportions.

The halo-substituted organic compound will bear an electrical charge, and by the terms "bear" or equivalent terms such as "bearing" or "borne," is meant that an electrical charge is associated with or adheres to each molecule of the compound and remains so as the compound travels through the electrophoretic system, whether such travel is by simple diffusion, convection, or electrophoretic migration, and is present at the pH of the buffer solution which the compound is suspended or dissolved. The electric charge can be that of a moiety that is part of the molecular structure of the compound, i.e., a moiety covalently bonded to the remainder of the compound. Examples of negatively charged moieties are carboxylates, phosphates, and sulfates. Specific examples of halo-substituted compounds bearing these moieties include, but are not limited to, trichloroacetate, tribromoacetate, iodoacetate, and trichloropropanoate. A negatively charged compound can be introduced into the buffer as desired, for example as a salt (e.g. sodium trichloroacetate) or as the conjugate acid (e.g. trichloroacetic acid). Examples of positively charged moieties are amino groups. Other examples of both types of moieties will be readily apparent to those of skill in the art. Alternatively, the electric charge can be imparted to the compound by a micelle incorporating or encapsulating the compound. A halo-substituted organic compound that is hydrophobic and/or nonpolar in character, or that is uncharged (non-ionized) at the pH of the buffer, can be encapsulated in a micelle formed from detergent molecules. Examples of uncharged compounds that can be used are chloroform, bromoform, iodoform, trichloroethanol, trichloroethane, 3-bromopropanol and trichloroacetamide. Examples of detergents that form negatively charged micelles are sodium dodecyl sulfate, sodium cholate, and sodium deoxycholate. An example of a detergent that forms a positively charged micelle is $C_{16}TAB$ (hexadecyl trimethylammonium bromide).

The electrode buffer into which the halo-substituted organic compound is placed will be the buffer in which the electrode of the same polarity will be immersed, so that the compound will migrate from that buffer into the gel when an electric potential is applied between the electrodes. Thus, when a compound bearing a negative charge is used, the compound will be placed in the cathode buffer, and when a compound bearing a positive charge is used, the compound will be placed in the anode buffer. A compound bearing an appropriate charge can be placed in a single electrode buffer or compounds bearing opposite charges can be placed in the two electrode buffers, although it will generally suffice to place a compound in one electrode buffer only. Use of the halo-substituted compound can be achieved without additional placement of the compound in either the sample itself prior to loading onto the gel, or in the gel prior to the commencement of electrophoresis.

In some embodiments, the anode and cathode are immersed in the same electrode buffer. Here, there can be two portions of electrode buffer, each covering one electrode, and the portions can be isolated from each other (such as by the gel), so that no molecules of halo-substituted compound, buffering agent, or water can freely pass between them. Alternatively, the portions can be connected, allowing the free passage of molecules and ions, or both electrodes can be immersed in the same portion of electrode buffer. Indeed, in some embodiments, the gel and other parts of the gel apparatus, as well as both electrodes, are all bathed in the same portion of electrode buffer, so that there is no segregation among the gel and electrodes. Such embodiments can be convenient to set up when the gel is oriented horizontally. When a single electrode buffer is used, it can contain one or more halo-substituted compounds of either charge, or a micelle-encapsulated halo-substituted compound, as discussed above.

The concentration of the halo-substituted compound in the buffer and the volume of the buffer can vary. Excess quantities of the halo-substituted compound will not affect the accuracy of the fluorescent signals or produce false fluorescent signals since only the product of the reaction between the halo-substituted compound and the protein (by way of the tryptophan residues) will generate a fluorescent signal. Nevertheless, for optimal results, the halo-substituted compound will be present in sufficient quantity to react either with all of the tryptophan groups in the proteins or with a proportion of the tryptophan groups that is approximately uniform throughout the gel. In either case, it is desirable that the signal be representative of the proteins present in the gel rather than the degree or pattern of penetration of the gel with the halo-substituted compound. Optimal concentrations and buffer solution volumes are readily determinable by those skilled in the art, for example by using routine experimentation on standard samples of known composition or by testing different concentrations and volumes on identical samples to determine those concentrations and/or volumes above which no further changes in the signal intensity and/or distribution are observed. In most cases, optimal results will be achieved with a halo-substituted compound at a concentration of from about 0.01% to about 5.0% on a volume/volume basis, and with a volume of electrode buffer (in which the compound is suspended or dissolved) of from about 1.0 to about 50.0 gel volumes. When sodium dodecyl sulfate or other micelle-forming detergent is present, its concentration may range from about 0.02% to about 5.0% on a weight/volume basis.

The electrode buffer(s) in which the halo-substituted compound is placed will generally contain a buffering agent to maintain its pH at a selected level, which can vary with the sample being analyzed or the proteins sought to be detected. Examples of buffering agents are lysine, arginine, histidine, 2-(N-morpholino)-ethanesulfonic acid (MES), N-(2-acetamido)-2-aminoethanesulfonic acid (ACES), piperazine-N, N'-2-ethanesulfonic acid (PIPES), 2-(N-morpholino)-2-hydroxy-propanesulfonic acid (MOPSO), N,N-bis-(hydroxyethyl)-2-aminoethanesulfonic acid (BES), 3-(N-morpholino)-propanesulfonic acid (MOPS), N-2- hydroxyethyl-piperazine-N-2-ethanesulfonic acid (HEPES), 3-(N-tris-(hydroxymethyl)methylamino)-2-hydroxypropanesulfonic acid (TAPSO), 3-(N,N-bis[2-hydroxyethyl]amino)-2-hydroxypropanesulfonic acid (DIPSO), N-(2-hydroxyethyl)piperazine-N'-(2-hydroxypropanesulfonic acid) (HEPPSO), 4-(2-hydroxyethyl)-1-piperazine propanesulfonic acid (EPPS), N-[tris(hydroxymethyl)-methyl]glycine (Tricine), N,N-bis(2-hydroxyethyl)glycine (Bicine), [(2-hydroxy-1,1-bis(hydroxymethyl)ethyl)amino]-1-propanesulfonic acid (TAPS), N-(1,1-dimethyl-2-hydroxyethyl)-3-amino-2-hydroxypropanesulfonic acid (AMPSO), tris(hydroxymethyl)amino-methane (Tris), and bis[2-hydroxyethyl]iminotris-[hydroxymethyl]methane (Bis-Tris). The pH can vary widely depending on the particular separation, but in most cases will fall within the range of about 3 to about 10, and in certain cases from about 4.5 to about 6.5, while in other cases from about 6.5 to about 9.0.

In some embodiments, a kit including one or more electrode buffers is provided. Each electrode buffer can include a halo-substituted organic compound and buffering agent as described above. The halo-substituted compound and buffering agent can be matched so that the compound bears a desired charge at or near the pKa of the buffering agent, or within the useful pH range of the buffering agent. The kit can be tailored to a specific electrode polarity, electrophoresis set-up, gel type, or biological sample type, as desired.

Any electrophoresis gel can be used in the methods described herein. For example, the gel can be of any dimensions, have any number of lanes, and be prepared (poured) by hand or by machine. In some embodiments, the gel comprises polyacrylamide, which can be present at any percentage or concentration, including at more than one concentration (e.g. in stacking and resolving portions of the gel) or at a gradient of concentrations. The gel can also comprise a denaturing agent such as sodium dodecyl sulfate (SDS), or one of the buffering agents listed above. Other common constituents of electrophoresis gels, particularly gels used to separate complex protein samples, will be apparent to the skilled artisan. In some cases, better separation of proteins, as well as more efficient transfer of the halo-substituted compound into the gel, can be achieved if the gel is similar in chemical composition (e.g., contains the same buffering agent) to the electrode buffer(s).

In some embodiments, the gel includes additives that allow proteins to migrate through the gel faster and at higher applied voltages than would be practicable in the absence of these additives. The additives also improve separation of proteins by preventing the duplication of bands, which can result from gaps or undesired interactions between the gel and any surfaces between which it is held (see e.g. U.S. Pat. No. 7,056, 426). Examples of such additives include poly(vinyl alcohol), agarose, poly(vinyl pyrrolidone), poly(ethylene glycol), poly(ethylene oxide), poly(propylene glycol), poly(propylene glycol)/poly(ethylene glycol) copolymers, and linear polyacrylamide. Electrophoresis gels containing one or more of these additives are available from Bio-Rad under the name 'TGX'.

The biological sample to be subjected to electrophoresis can be obtained from any source. Examples of potential sources include cells, groups of cells, tissues, or entire organisms, living or dead. The sample can be a cell lysate, tissue homogeneate, or sample of blood, saliva, urine, cerebrospinal fluid, or other bodily fluid, among other possibilities. It will be appreciated that samples from different sources vary in the number, identities, and abundances of proteins that they contain, and that many of these parameters will not be known at the time the sample is acquired. As is well known, gel electrophoresis can be used to analyze complex protein samples and compare these samples with each other. Comparisons can be made between samples from different biological sources, such as different adult humans, humans of different ages, diseased and healthy humans, humans of different races or ethnicities or from different parts of the world, humans undergoing different treatments for diseases, humans undergoing treatments vs. humans not undergoing treatments, humans vs. non-human mammals, or any variable vs. a control. Other examples will be readily apparent to those of skill in the art.

The number of different proteins that will most often be present in a "complex sample" as the term is used herein will be about 50 or more, often within from about 50 to about 100,000, and in many cases from about 100 to about 50,000. The molecular weights of these proteins can vary widely, and many such samples will have molecular weights ranging from those having less than twenty amino acid residues to those having 1,000 or more, including as many as 5,000.

Likewise, the number of tryptophan residues among the proteins in a single sample can range from as little as zero to as high as 5%.

Once obtained, a biological sample may require preparation before it can be run on an electrophoresis gel and detected. Such preparation can include e.g. centrifuging or filtering the sample to remove tissue fragments, membranous structures, or other large contaminants; concentrating the sample into a smaller volume by application of a pressure differential; or adding chemicals to the sample such as protease inhibitors or buffering agents. In particular, in some embodiments the sample is added to or resuspended in a buffer similar to the electrode buffer(s) in terms of pH, salt concentration, buffering agent, or other characteristics. This ensures that proteins of the sample will enter the electrophoresis gel and migrate within it in an efficient, reproducible manner. Other preparatory steps will be apparent to those skilled in the art. It will be appreciated that some preparatory steps can reduce the number of proteins loaded onto the electrophoresis gel and later reacted with the halo-substituted compound.

The electrophoresis gel can be run using any techniques desired, and using any available materials or apparatus. In standard practice, the gel is contacted with the electrode buffer(s) and placed between two electrodes, which are energized to opposite polarities. The resulting electric field between the electrodes drives electrophoresis and causes the halo-substituted compound(s) to enter the gel from the electrode buffer(s). During electrophoresis or "running", proteins that have been loaded in the gel migrate within the gel, away from the site of loading, and become separated from each other according to molecular weight, size, or charge. Electrophoresis can also separate proteins from contaminants that may have been loaded onto the gel along with the protein sample. Such contaminants can fail to enter the gel when the potential difference is applied, can diffuse from the gel into the surrounding buffer, or can pass through the gel more slowly or quickly than proteins of interest in the sample. For convenience and if desired, a molecular weight marker can be loaded into the gel along with the protein sample, allowing the practitioner to track the positions of proteins in the sample during or after migration.

Once the proteins and the halo-substituted compound have been distributed through the gel by electrophoresis, the gel is irradiated with ultraviolet light to cause the reaction between the compound and the tryptophan residues to occur. The irradiation intensity and duration can vary, provided that the intensity and duration are both sufficient to cause the reaction to occur and to produce a fluorescent emission that can be detected and quantified. Exposure and detection can occur simultaneously. Optimum intensities and durations can be determined by routine experimentation combined with simple observation of the resulting image. The manner of detection and quantification may vary with the type of detector used. Irradiation wavelengths within the range of from about 200 nm to about 400 nm, and exposure times of from about thirty seconds to about thirty minutes, or in many cases from about 1 minute to about ten minutes, will generally provide adequate results. Irradiation can be achieved by either transillumination or epi-illumination, and detection can be achieved by imaging such as by the use of photography, or by electronic sensors such as photodiodes, CCD detectors, or CMOS detectors. Digital results can be analyzed by conventional imaging software. Irradiation can be repeated after the coupling reaction has occurred, for repeat detections.

The halo-substituted compounds used in the practice of the present invention are preferably used in the absence of any protein stains so that the procedure is truly stain-free. By "protein stains" is meant compounds that are color-bearing or fluorescent on their own, i.e., in the absence of any reaction with amino acid residues, and that adhere to proteins by means other than a coupling reaction. Many such stains exist, examples of which, as noted above, are COOMMASSIE™ Brilliant Blue, Ponceau S, and SYPRO RUBY™.

The electrophoretic procedures described herein can be used in any of the many forms of electrophoresis, including one-dimensional slab or capillary electrophoresis, two-dimensional electrophoresis, and isoelectric focusing. All electrophoretic procedures can be performed in conventional ways commonly used in the laboratory and well known in the art, including loading samples onto a gel, the arrangement and use of electrodes and electrode buffers and the energizing of the electrodes a the appropriate polarities.

If desired, after introducing a halo-substituted organic compound into the gel during electrophoresis and reacting the compound with proteins of the biological sample, the proteins can be transferred out of the gel and then detected. Transfer can be accomplished using electroblotting. In some embodiments, detection is then performed using an amino acid sequence within the protein that can be recognized with high affinity and specificity by a binding partner. Such a sequence is called a recognition sequence in the art, and binding partners can include antibodies, other proteins, or small molecules. Alternatively, or in addition, proteins can be detected outside the gel using the fluorescence of tryptophan residues that have already reacted with the halo-substituted organic compound.

Electroblotting involves the transfer of proteins out of an electrophoresis gel after the gel has been run, by applying an electric field to the gel in a direction orthogonal to that used for running The transferred proteins are deposited onto the surface of a membrane (also called a 'blot' or 'blotting membrane'; typically made of nitrocellulose or polyvinylidene fluoride (PVDF)), which can then be incubated in a solution containing the binding partner. Binding between the recognition sequence and binding partner can be detected optically, for example using fluorescence or chemiluminescence, with radioactivity, or with other means known in the art. The blotting membrane can also be exposed to UV light, and fluorescence arising from reacted tryptophan residues in proteins on the membrane can be detected as described above or using established methods.

The general method of placing one or more halo-substituted organic compounds in electrode buffer(s) used for electrophoresis, transferring the compounds into the gel during electrophoresis, and reacting the compounds with tryptophan residues of proteins in the gel, can be used to quantify the amount of protein in a biological sample or normalize the amounts of proteins in one or more biological samples to each other. Such quantification or normalization can be performed whether proteins containing reacted tryptophan residues are detected in the gel, on a blotting membrane, or elsewhere. Further description of protein quantification and normalization using stain-free methods is provided in co-pending U.S. patent application Ser. No. 13/870,710.

EXAMPLE

To demonstrate different methods of contacting proteins with halo-substituted organic compounds in polyacrylamide gels, four gels (A-D) were loaded with protein samples and run.

Gel A was a 4-20% Criterion™ TGX™ Stain-Free Precast Gel (Bio-Rad Cat. No. 567-8094). This gel contained 0.5% trichloroethanol, which was incorporated into the gel upon pouring, i.e. at the time of manufacture. Gels B, C, and D were 4-20% Criterion™ TGX™ Precast Gels (Bio-Rad Cat. No. 567-1094). These gels were not poured (i.e. manufactured) with any halo-substituted organic compound.

Each gel was inserted vertically into a Bio-Rad Criterion™ cell filled with electrode buffer. In the case of Gels A and D, the cell was filled with 900 mL 1× TGS (Tris/glycine/SDS) running buffer (Bio-Rad Cat. No. 161-0732). In the case of Gel B, the cell was filled with buffer containing 0.5% v/v trichloroethanol (900 mL 1× TGS running buffer plus 4.5 mL trichloroethanol, Sigma-Aldrich Cat. No. T54801-100G). In the case of Gel C, the cell was filled with buffer containing 0.5% v/v trichloroacetic acid (900 mL 2× TGS running buffer plus 4.5 mL trichloroacetic acid, VWR Cat. No. BDH3372-2). For each gel, the same electrode buffer was used to submerge both the anode and the cathode, although each electrode was covered by a separate portion of buffer.

The gels were loaded with protein samples prepared from the Bio-Rad SDS-PAGE Standards (Bio-Rad Cat. No. 161-0317). First, a stock solution of protein was prepared by diluting Bio-Rad SDS-PAGE Standards 1:10 in 1× Laemmli sample buffer (50% 2× Laemmli sample buffer (Bio-Rad Cat. No. 161-0737), 45% water, and 5% 2-mercaptoethanol (Bio-Rad Cat. No. 161-0710)). Serial dilutions of the stock solution (1:2, 1:4, 1:8, 1:16, 1:32, 1:64, 1:128, 1:256, 1:512) were then prepared in 1× Laemmli sample buffer. The stock solution was loaded into lane 1 of each gel, and dilutions thereof were loaded into lanes 2-10. Thus, the total protein concentration in each lane differed by a factor of two from the concentration in the adjacent lane(s), with the concentrations decreasing going from lane 1 to lane 10.

After loading, each gel was run for 30 minutes at 250 V and imaged using the ChemiDoc MP system. The imaging involved irradiating the gel with UV light and detecting emitted fluorescence.

Figure 2:
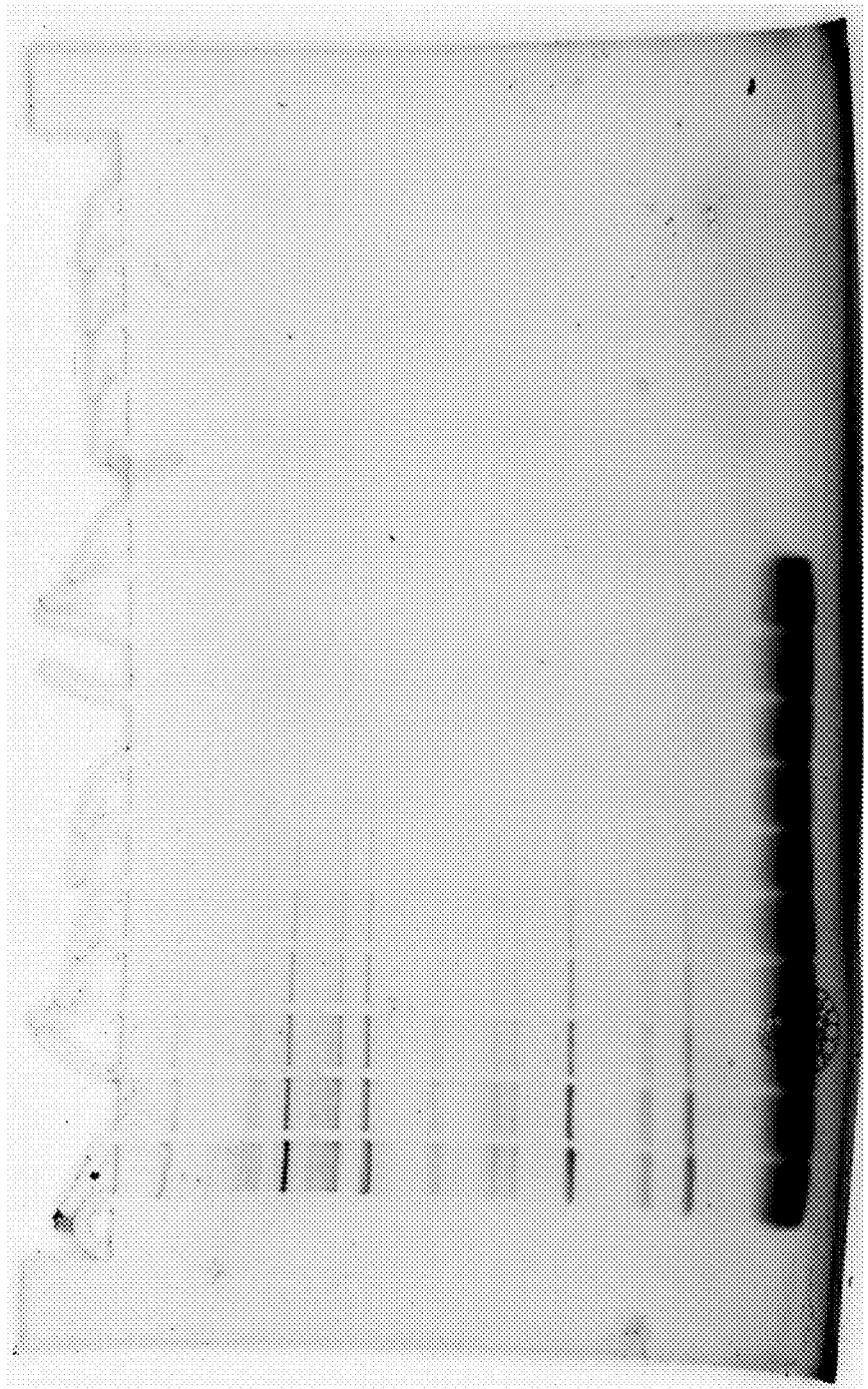
FIG. 2 shows fluorescence emitted by proteins in Gel B of the Example. No halo-substituted organic compound was incorporated into the gel upon pouring, but electrophoresis was carried out in the presence of an electrode buffer containing 0.5% trichloroethanol.
Figure 3:
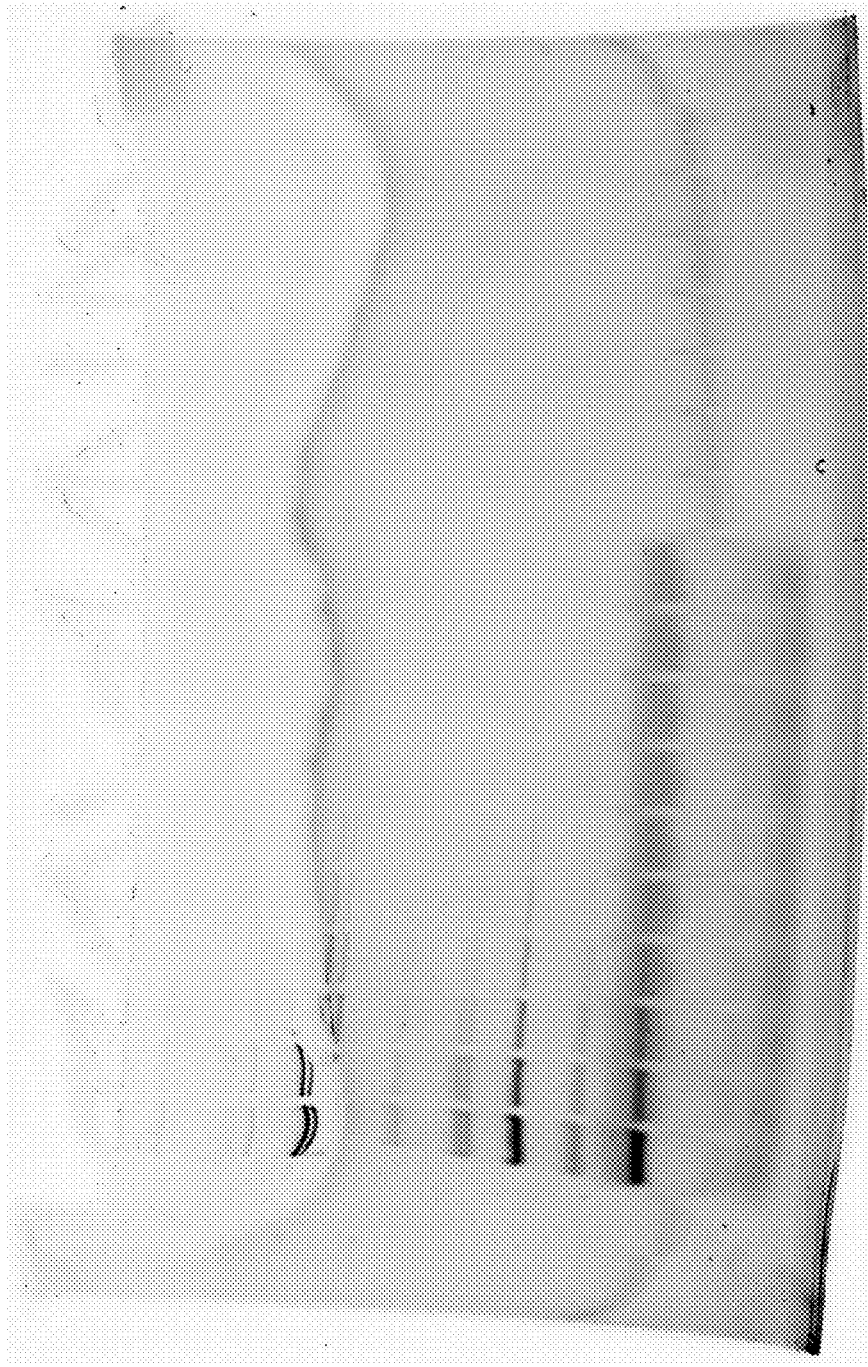
FIG. 3 shows fluorescence emitted by proteins in Gel C of the Example. No halo-substituted organic compound was incorporated into the gel upon pouring, but electrophoresis was carried out in the presence of an electrode buffer containing 0.5% trichloroacetic acid.
Figure 4:
FIG. 4 shows fluorescence emitted by proteins in Gel D of the Example. No halo-substituted organic compound was incorporated into the gel upon pouring or present in the electrode buffer during electrophoresis.

The fluorescence of Gel A (FIG. 1) demonstrates that proteins came into contact with trichloroethanol that was incorporated into the gel upon pouring. The fluorescence of Gels B (FIG. 2) and C (FIG. 3) demonstrates that proteins came into contact with trichloroethanol and trichloroacetate, respectively, that entered the gel from the electrode buffer during electrophoresis. Gel D (FIG. 4) exhibited significantly less fluorescence than the other gels because no halo-substituted organic compound was incorporated into the gel upon pouring or present in the electrode buffer. Fluorescence emitted from Gel D was likely the auto-fluorescence of aromatic amino-acid side-chains (see e.g. Roegener et al., Analytical Chemistry 75, pp. 157-159, 2003).

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method for separating proteins contained within a biological sample by electrophoresis in a gel along a linear dimension between first and second ends of said gel and detecting said proteins so separated, said method comprising:
   (a) loading said sample onto said gel and electrically connecting said first and second ends of said gel with electrodes through electrode buffers in which said electrodes are immersed, wherein at least one of said electrode buffers has suspended therein a halo-substituted organic compound that covalently reacts with tryptophan residues upon irradiation with ultraviolet light to form fluorescent compounds, said halo-substituted organic compound bearing a negative charge,
   (b) energizing said electrodes to opposing polarities in a direction selected to cause said proteins to distribute within said gel along said linear dimension and to cause said halo-substituted organic compound to migrate into said gel from said electrode buffer, wherein said electrode that is immersed in said electrode buffer in which said halo-substituted organic compound is suspended is energized as a cathode, and
   (c) with said proteins so distributed and said halo-substituted organic compound having so migrated into said gel, irradiating said gel with ultraviolet light to react tryptophan residues on said proteins with said halo-substituted organic compound to form fluorescent derivatives of said proteins and detecting fluorescent signals emitted from said fluorescent derivatives.

2. The method of claim 1 wherein said halo-substituted organic compound has a molecular structure that contains a negative ionic moiety.

3. The method of claim 1 wherein said halo-substituted organic compound is a hydrophobic compound encapsulated in a negatively charged micelle.

4. The method of claim 3 wherein said micelle is formed of sodium dodecyl sulfate.

5. The method of claim 1 wherein said halo-substituted organic compound has a molecular weight of 200 or less.

6. The method of claim 1 wherein said halo-substituted organic compound is trichloroacetic acid.

7. The method of claim 2 wherein said halo-substituted organic compound is selected from the group consisting of trichloroacetate, tribromoacetate, iodoacetate, and trichloropropanoate.

8. The method of claim 3 wherein said halo-substituted organic compound is selected from the group consisting of chloroform, bromoform, iodoform, trichloroethanol, trichloroethane, 3-bromopropanol and trichloroacetamide.

9. The method of claim 8 wherein said halo-substituted organic compound is trichloroethanol.

10. A method for separating proteins contained within a biological sample by electrophoresis in a gel along a linear dimension between first and second ends of said gel and detecting said proteins so separated, said method comprising:
    (a) loading said sample onto said gel and electrically connecting said first and second ends of said gel with electrodes through electrode buffers in which said electrodes are immersed, wherein at least one of said electrode buffers has suspended therein a halo-substituted organic compound that covalently reacts with tryptophan residues upon irradiation with ultraviolet light to form fluorescent compounds, said halo-substituted organic compound bearing a positive charge,
    (b) energizing said electrodes to opposing polarities in a direction selected to cause said proteins to distribute within said gel along said linear dimension and to cause said halo-substituted organic compound to migrate into said gel from said electrode buffer, wherein said electrode that is immersed in said electrode buffer in which said halo-substituted organic compound is suspended is energized as an anode, and
    (c) with said proteins so distributed and said halo-substituted organic compound having so migrated into said gel, irradiating said gel with ultraviolet light to react tryptophan residues on said proteins with said halo-substituted organic compound to form fluorescent derivatives of said proteins and detecting fluorescent signals emitted from said fluorescent derivatives.

11. The method of claim 10 wherein said halo-substituted organic compound has a molecular weight of 200 or less.

12. The method of claim 10 wherein said halo-substituted organic compound is a hydrophobic compound encapsulated in a positively charged micelle.

13. The method of claim 12, wherein said micelle is formed of hexadecyl trimethylammonium bromide ($C_{16}$TAB).

14. The method of claim 12 wherein said halo-substituted organic compound is selected from the group consisting of chloroform, bromoform, iodoform, trichloroethanol, trichloroethane, 3-bromopropanol and trichloroacetamide.

15. The method of claim 14 wherein said halo-substituted organic compound is trichloroethanol.

16. The method of claim 10 wherein said halo-substituted organic compound has a molecular structure that contains a positive ionic moiety.

17. The method of claim 16 wherein said positive ionic moiety is an amino group.

* * * * *